United States Patent [19]

Taylor et al.

[11] 4,449,927
[45] May 22, 1984

[54] DENTAL BITE RELATOR

[76] Inventors: James C. Taylor, P.O. Box 1019; Leonard B. Barber, Jr., 820 Fleming St., both of Hendersonville, N.C. 28793

[21] Appl. No.: 355,383

[22] Filed: Mar. 8, 1982

[51] Int. Cl.³ .............................................. A61C 9/00
[52] U.S. Cl. .......................................... 433/38; 433/45
[58] Field of Search ...................... 433/38, 37, 41, 43, 433/45, 46

[56] References Cited

U.S. PATENT DOCUMENTS

| | | | |
|---|---|---|---|
| 1,360,146 | 11/1920 | Ragatz | 433/41 |
| 1,584,092 | 5/1926 | Harris | 433/38 |
| 1,979,493 | 11/1934 | Salvio | 433/38 |
| 2,597,929 | 5/1952 | Gorsky et al. | 433/37 |
| 2,634,500 | 4/1953 | McAdoo | 433/38 |
| 3,085,337 | 4/1963 | Shulman | 433/38 |
| 3,501,837 | 3/1970 | Clark | 433/38 |
| 4,204,323 | 5/1980 | Neubert et al. | 433/38 |
| 4,251,209 | 2/1981 | Bekey et al. | 433/37 |
| 4,299,574 | 11/1981 | Neihart | 433/37 |

FOREIGN PATENT DOCUMENTS 2459652  2/1981  France ................................ 433/37

Primary Examiner—John J. Wilson
Attorney, Agent, or Firm—Peck & Peck

[57] ABSTRACT

A dental instrument for simultaneously taking an impression and a bite has a pair of parallel elongated bite tray holders which are laterally spaced apart and are connected together at one of their adjoining ends by a connector wire loop. A manipulating handle is fixed to one of the tray holders at the end opposite to its connected end and has an inner fixed leg portion which protrudes from the instrument at a close obtuse angle to pass the lip of a patient and has an integral free outer end portion that extends from the inner end at a sharp angle of at least 90° for easier manipulation beyond the cheek of the patient by an operator. A bite tray is removably and slidably carried by and positioned between the tray holders.

1 Claim, 5 Drawing Figures

U.S. Patent  May 22, 1984  4,449,927
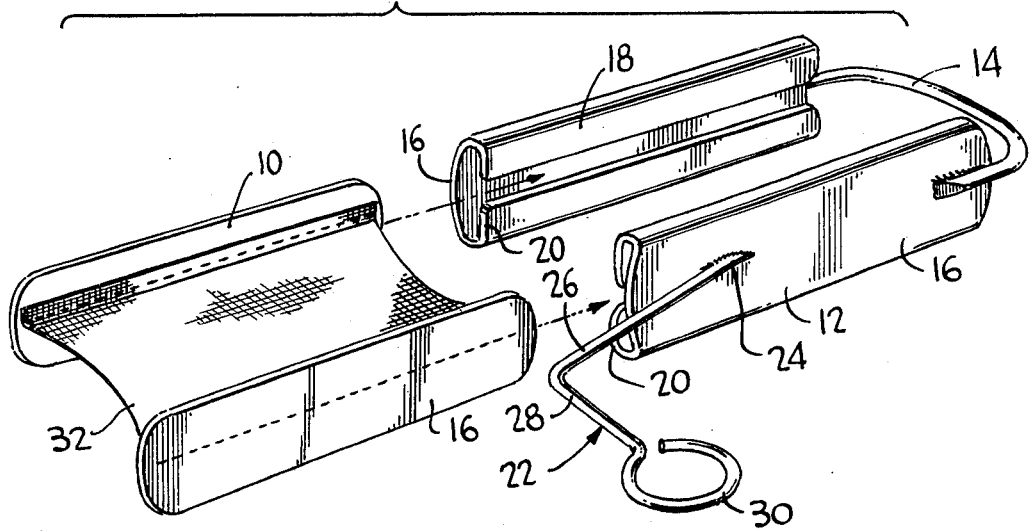
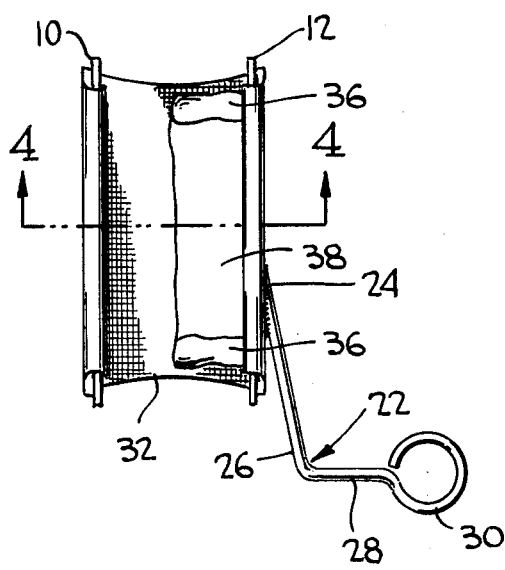
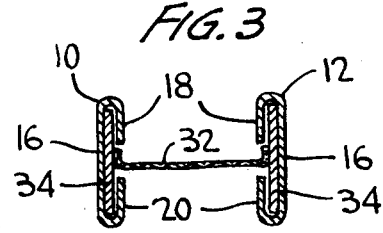
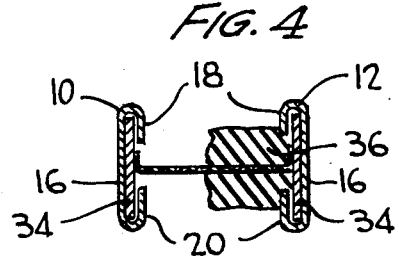
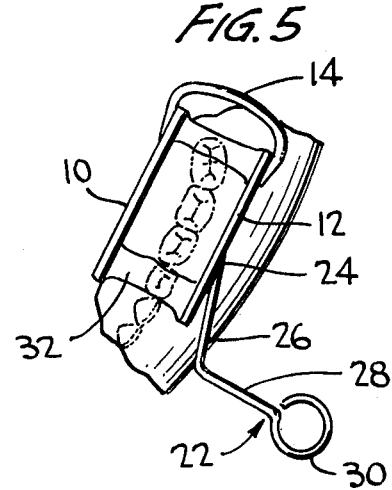

DENTAL BITE RELATOR

This invention relates broadly to the art of dentistry and, more specifically, relates to an instrument by means of which an impresion can be taken of teeth in preparation for receiving crowns, inlays, and the like, while simultaneously taking and recording, in the impression material, the bite or registration between opposing arch quandrants.

The primary object of this invention is to establish unilateral centric relation of opposing arch quadrants while, at the same time and simultaneously therewith, taking an impression of decayed teeth which have been prepared by the dentist. This highly desirable single operation to achieve dual results has been attained by the development of a unique instrument which is easy to use and may be produced inexpensively, has no moving parts and will remain in service through a great many of such single operations.

It is now conventional practice in the dental technological field, when a tooth or teeth become decayed, to grind away the decayed part of the tooth or teeth, and by such granding, to reshape the teeth to receive, for instance, an inlay, crown or the like dental component. After the dentist has reworked the decayed teeth, as briefly outlined above, and prior to making the inlays, crowns or the like, it is now customary practice to make an impression of the prepared teeth and, of course, it will be evident that this impression must be accurate. After this impression is taken, the dentist takes a registration of the bite, which shows the position of the opposing teeth in relation to the prepared teeth. Thus, it will be apparent that in current dental technology, a separate impression tray must be used to take the impression, and then a separate bite, registration or occlusion is taken.

It will now be recognized that prior to the present invention, two separate steps were necessary to obtain the desired result. In this present practice and procedure, the bite impression must be fitted to the model of the first impression which is taken, and this operation usually results in an inaccuracy which necessitates the making of adjustments to the finished crowns or inlays in the mouth.

Not only does the present practice, as discussed above, result in many inaccuracies, but it also is time consuming for the dentist, and, furthermore, difficult and unpleasant for the patient.

One of the further and significant purposes of this invention is to develop an instrument which provides an arrangement whereby this dual result may be obtained in a single operation by means of one instrument, wherein the instrument is so constructed as to substantially expedite and ease the dentist's task in simultaneously taking an impression and a bite and to also make this operation easier and less distasteful to the patient being operated on.

With the foregoing general objects, features and results in view, as well as certain others which will be apparent from the following explanation, the invention consists in certain novel features in design, construction, mounting and combination of elements, as will be more fully and particularly referred to and specified hereafter.

FIG. 1 is a perspective view of the invention.
FIG. 2 is a top plan view.
FIG. 3 is an end elevational view.
FIG. 4 is a cross-sectional view, taken on line 4—4 of FIG. 2.
FIG. 5 is a perspective view showing the invention in use in its placement in the mouth of a patient.

The dental bite relator instrument which we have devised and which permits the simultaneous taking of an impression and a bite, comprises a pair of substantially parallel, laterally, spaced-apart bite tray holders which are designated in their entirety by the numerals 10 and 12. These bite tray holders 10 and 12 are connected together at one of their adjoining ends by means of an arcuate wire element 14 which is fixed to a complimentary end of each of the bite tray holders 10 and 12. The arcuate connecting element 14 is formed from any suitable type of spring metal or the like, more or less flexible or springy material, so that the bite tray holders 10 and 12 have a degree of adjustability toward and from each other.

It is to be noted, and it is of some significance in the use of the instrument by the dentist, that the ends of the arcuate connecting element 14 are fixed, as by welding or in any suitable manner, to the tip ends of the bite tray holders or supporting members 10 and 12, and it should also be noted that while the major portion of the arcuate connecting member 14 is substantially semi-circular in shape, it is preferable, though not necessary, that the ends of the connecting element 14, adjacent to their connection to the bite tray holders 10 and 12, be more or less parallel with the holders.

Each bite tray holder or supporting member 10 and 12 is composed of an elongated flat plate 16 forming the exterior thereof, and the top and bottom longitudinal edges of each plate are rolled or formed with inner flanges which are inwardly spaced from the plates, the upper flange 18 depending downwardly from the upper longitudinal edge of the plate 11, while the lower flange 20 extends upwardly from the lower longitudinal edge of each plate 16, the opposing longitudinal edges of the flanges 18 and 20 being spaced apart for a purpose to be hereinafter described. It will thus be apparent that a guide or track member is provided on each bite tray holder or supporting member 10 and 12.

The instrument is provided with a handle designated generally by the numeral 22. This handle is fixed, in any suitable manner, to one of the supporting members 10 or 12 at an exterior point thereon, adjacent to but removed from the end of the supporting member opposite to that from which the connecting elements 14 extends, as at 24. The handle 22 includes an inner leg portion 26 which extends from the bite tray holder to which it is affixed at an obtuse angle with respect thereto which is on the order of about 10° and the fixed inner leg portion terminates in an outer leg portion 28 which extends at a sharp angle of at least 90° from the inner leg portion and terminates at its free outer end in an integral loop 30 that defines a handle for ease of manipulation of the instrument by the dentist. Consideration of the drawings clearly indicates that the outer leg portion and the handle extend beyond the posterior end of the body of the instrument, while the connector element 14 extends beyond the anterior end of the body of the instrument. The handle is formed in one piece from rigid rod-like material.

The instrument of this invention has a bite tray which consists of a body of gauze or the like material 32, which is of a width transversely extending between the supporting members substantially the same as the transverse distance between the flanges 18 and 20 on the bite tray supporting members 10 and 12, and is of a length which is preferably somewhat shorter than the length of the bite tray supporting members. The longitudinal edges of the gauze body 32 of the bite tray are fixed in any suitable manner centrally along cardboard or the like relatively stiff material supporting borders, edges or rims 34. The supporting edges 34 are of a width so as to have a sliding fit within the flanges 18 and 20 of each bite tray holder 10 and 12.

It will now be appreciated that when the instrument is to be used, the bite tray is positioned in the instrument by sliding the stiffened edges 34 thereof between the flanges 18 and 20 until the gauze web or body 32 which extends therebetween is positioned substantially as disclosed in FIG. 1 of the drawings. Thus, the gauze web or body will extend between the bite tray holders or supporting members, and is ready to receive the impression material in a manner as will be hereinafter described.

In the use of this invention, to simultaneously take the impression and the bite, the bite tray is inserted into position as disclosed in FIG. 1 of the drawings by sliding the stiffened borders 34 thereof into the open ends of the bite tray holders 10 and 12, whereupon the gauze web 32 will extend across and between the bite tray holders, such gauze extending outwardly between the area provided between the opposing edges of the flanges 18 and 20.

When the bite tray is positioned as described and as shown in FIG. 1 of the drawings, a border or wall of postdam wax is placed on each side of the gauze 25 at the anterior and posterior borders thereof, such walls of postdam wax being designated by the reference numeral 36. Postdam wax is a soft utility wax which functions generally to seal and area and is a term conventionally used in the dental art. After the walls 36 are applied along the posterior and anterior edges of the gauze on both sides thereof, the gauze between such walls of wax is loaded with a heavy rubber base material on both sides thereof, such heavy rubber base material being disclosed at 38 in the drawings.

Such the decayed teeth have been prepared by the dentist as described above, he then injects a free flowing rubber base material over the prepared surfaces of the teeth, and this may be accomplished by using a large rubber base syringe which eliminates the trapping of air and reduces air bubbles in the finished impression. When the injectable rubber base material has been applied to the prepared teeth, the patient then opens his mouth wide and the instrument with the heavy rubber base thereon is inserted into the mouth with the dentist holding the handle 30 thereof, the connector element 14 constituting the forward part of the instrument in this operation. The instrument is, of course, placed with one side thereof, that is one side of the coated gauze web, over the prepared teeth with the rubber base material applied thereto, the opposite side of the gauze of the bite tray being directed toward the teeth which are opposite the prepared teeth. The patient then closes his mouth to receive the arch which opposes the prepared teeth, so as to form both the impression and the bite relationship simultaneously. It is usual to have the patient hold his mouth firmly closed for approximately ten minutes prior to a careful removal of the tray.

Upon removal of the tray, the disc areas are poured first, and then the dentist uses a conventional technique for Neys dowell pins. He then mounts the impression and the bite on an articulator and it is allowed to harden for approximately two hours.

The results obtained by using this instrument and following this technique will be an accurate impression of prepared teeth plus perfect centric occlusion with the opposing arch.

It will be understood that the soft postdam wax walls 36 provide a more individualized relator and also function to hold the rubber base material 38 in proper position to thereby prevent excessive flowing of the rubber base.

It will now be recognized by consideration of the drawings and the description of this invention that substantial advantages are obtained in the use of the instrument by having the handle thereof project at the stated and shown angle to the longitudinal axes of the bite tray holders to extend a distance rearwardly of the instrument. This enables the instrument to be more easily inserted into the mouth of the patient and also permits greater ease of manipulation by the dentist. The inner end of the handle protrudes at a slight obtuse angle from the instrument to conveniently and comfortably pass the lip of a patient, as shown in FIG. 5, while the outer end portion extends at a sharp angle from the patient's cheek and beyond for easier manipulation from the cheek by the operator. This allows for better control by the operator without interference of the lips or cheeks of the patient.

Advantages also flow from the particular construction of the connecting element at the end portions thereof of the tray holders. Partial straightening of these end portions prevents the connecting element 14 from pressing too tightly against the inner cheek area of the patient to thereby reduce substantially any pain or unpleasantness possibly felt by the patient.

What is claimed is:

1. A dental instrument for simultaneously taking an impression of prepared teeth and the bite registration thereof with respect to the arch quadrants opposing said prepared teeth comprising a pair of parallel laterally spaced apart, oppositely disposed elongated bite tray holders adapted to hold and support a bite tray therebetween, each of said bite tray holders having inner elongate faces provided with a longitudinally extending channel, said channels being open at each end and disposed in facing relation to receive a portion of a bite tray, an arcuate wire member fixed to and extending between complementary ends of the bite tray holders outwardly thereof for maintaining them in spaced apart, oppositely and complementarily disposed relation, said tray holders having outer faces and a one-piece handle member angularly projecting from and fixed to the outer face of one tray holder adjacent its end opposite the end connected to the other tray holder, said handle member having an inner end portion fixed to and projecting forwardly and only slightly angularly outwardly from its associated tray holder and having an outer end portion disposed at an acute angle to the inner end portion said handle member being a one-piece rod-like element with the outer end portion of the handle member being disposed substantially at a right angle to the inner end portion which is fixed to the associated tray holder at a slight obtuse angle thereto.

* * * * *